US00PP34235P2

(12) United States Plant Patent
Bradford et al.

(10) Patent No.: US PP34,235 P2
(45) Date of Patent: May 17, 2022

(54) PLUM TREE NAMED 'PLUMRED II'

(50) Latin Name: *Prunus salicina*
Varietal Denomination: Plumred II

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,907

(22) Filed: Dec. 17, 2021

(51) Int. Cl.
*A01H 5/08* (2018.01)
*A01H 6/74* (2018.01)

(52) U.S. Cl.
USPC ..... Plt./184

(58) Field of Classification Search
USPC ..... Plt./184
See application file for complete search history.

(56) References Cited

U.S. PATENT DOCUMENTS

PP23,718 P3 7/2013 Bradford

*Primary Examiner* — Susan McCormick Ewoldt

(57) ABSTRACT

The present invention relates to a plum tree, *Prunus salicina*, and more particularly to a new and distinct variety broadly characterized by a small size, moderately vigorous, hardy, and productive tree. Being self-unfruitful, the present variety requires cross pollination from an apricot, interspecific, or plum that blooms during the mid season, such as 'Blackred III' (U.S. Plant Pat. No. 18,668) interspecific tree. The present variety produces a heavy amount of flowers that produce an abundance of pollen to entice good bee activity to facilitate pollination. The fruit matures under the ecological conditions described during mid June, with first picking on Jun. 14, 2021. The fruit is medium to large in size, dark purplish red in skin color, full dark red in flesh color, clingstone in type, oblate in shape, firm in texture, juicy, moderately sweet, and very good in flavor.

1 Drawing Sheet

Botanical classification: *Prunus salicina.*
Varietal denomination: 'PLUMRED II'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'Plumred II'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2011 one such house containing 'Blackred VI' interspecific tree (U.S. Plant Pat. No. 23,718) was crossed by us in this manner. To pollinate this interspecific tree, we selected bouquets from several sources of plum trees without keeping specific written details. Upon reaching maturity the fruit from this interspecific tree was harvested, and the seeds were removed, cracked, stratified and germinated as a group with the label "H1". They were grown as seedlings on their own root in our greenhouse, and upon reaching dormancy they were grafted as a group onto two year old rootstocks located in a cultivated area of our experimental orchard located near Le Grand, Calif. in Merced County (San Joaquin Valley). During the summer of 2014 the claimed variety was selected by us as a single tree from the group described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is most similar to its seed parent, 'Blackred VI' interspecific tree (U.S. Plant Pat. No. 23,718), by being self-unfruitful and by producing fruit that is dark purplish red in skin color, that is oblate in shape, that is clingstone in type, that is firm in texture, and that is very good in flavor, but is distinguished therefrom by blooming in the mid season instead of early season and by producing fruit that is larger in size, that is much darker red in flesh color, and that matures about 7 days earlier.

SUMMARY OF VARIETY

The present plum variety is characterized by a small size, moderately vigorous, hardy, and productive tree. Being self-unfruitful, the present variety requires cross pollination from an apricot, interspecific, or plum that blooms during the mid season, such as 'Blackred III' (U.S. Plant Pat. No. 18,668) interspecific tree. The present variety produces a heavy amount of flowers that produce an abundance of pollen to entice good bee activity to facilitate pollination. The fruit matures under the ecological conditions described during mid June, with first picking on Jun. 14, 2021. The fruit is medium to large in size, dark purplish red in skin color, full dark red in flesh color, clingstone in type, oblate in shape, firm in texture, juicy, moderately sweet, and very good in flavor.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jun. 19, 2021, on the original tree during its tenth growing season. The flower and bud descriptions were developed during the previous blooming season. All major color code designations are by reference to the Inter-Society Color Council, National Bureau of Standards. Common color names are also used occasionally.

PARENTAGE

Seed parent: 'Blackred VI' (U.S. Plant Pat. No. 23,718) interspecific tree.

Pollen parent: Unknown plum.

TREE

Size: Small, reaching and maintaining a height of 8' [2.44 m.] and a spread of 6' [1.83 m.] after ten growing seasons utilizing typical dormant pruning.

Vigor: Moderately vigorous, responding typically to irrigation and fertilization. The variety grows about 2' [0.61 m.] of surplus top-growth during the spring and summer. The plant should be grown on a standard commercial rootstock for production purposes.

Growth: Upright and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming apricot, interspecific, or plum, such as 'Blackred III' (U.S. Plant Pat. No. 18,668) interspecific tree.

Bearing: Regular bearer, weather dependent, no crop failures observed as of yet.

Trunk:

*Size.*—Medium, reaching a maximum diameter of 4½" [114 mm.] after the tenth growing season.

*Texture.*—Medium to shaggy.

*Bark color.*—A Grayish yellowish brown [80. gy.yBr] and Dark grayish yellowish brown [81. d.gy.yBr] variegation with Moderate yellowish brown [77. m.yBr] crevices present.

*Lenticels.*—Approximate Number Per Square Inch: 15. Color: Light brownish gray [63. l.brGy]. Average Size: ¼" [6.4 mm.] in length. The width is typically one fourth as much as the length. Shape: Elongated.

Branches:

*Size.*—Stocky, scaffold diameter is 2¼" [57.2 mm.] measured 12" above the crotch, limb diameter is 1½" [38.1 mm.] measured 12" above the first fork.

*Texture.*—Smooth to medium on first and second year wood, increasing in roughness with age.

*Color.*—1st Year Wood Topside: Grayish red [19. gy.R]. 1st Year Wood Underside: Brilliant yellow green [116. brill.YG]. Older Wood: A Grayish yellowish brown [80. gy.yBr] and Moderate yellowish brown [77. m.yBr] variegation with Dark grayish yellowish brown [81. d.gy.yBr] crevices present.

*Lenticels.*—Number Per Square Inch: About 20 on second year wood. Color: Strong yellowish brown [74. s.yBr]. Average Size: Small, 1/16" [1.6 mm.] in length. The width is typically one fourth as much as the length. Shape: Elongated.

Leaves:

*Size.*—Medium. Average Length: 3 11/16" [93.7 mm.]. Average Width: 1¾" [44.5 mm.].

*Arrangement.*—Alternate.

*Thickness.*—Medium.

*Form.*—Elliptical.

*Apex.*—Acuminate.

*Base.*—Acute with an average base angle of 75 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ¾" [19.1 mm.]. Average Thickness: 1/16" [1.6 mm.]. Color: Pale greenish yellow [104. p.gY] with some Grayish red [19. gy.R] areas where exposed toward the sun.

*Stipules.*—Number: Mostly 2 per leaf, up to 6 per growing tip. Average Length: ¼" [6.4 mm.]. Color: Light yellow green [119. l.YG] becoming Moderate olive [107. m.Ol] with age.

*Glands.*—Number: Mostly 2 per leaf. Position: Slightly alternate, positioned at the intersection of the petiole and base of leaf blade. Form: Globose. Size: Medium, 1/32" [0.8 mm.] in diameter. Color: Grayish greenish yellow [105. gy.gY] becoming Grayish red [19. gy.R] in the center with age. Leaf buds: Pointed.

Flower buds:

*Hardiness.*—Hardy with respect to central California blooming season.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Very slightly pubescent.

*Tip color.*—White [263. White].

Flowers: Perfect, complete, perigynous, usually a single pistil, typically thirty or more stamens, five sepals and petal locations alternately positioned.

*Average flower diameter.*—1¼" [31.8 mm.].
*Average flower depth.*—5/16" [7.9 mm.] when fully open.
*Average pedicel length.*—⅜" [9.5 mm.].
*Number of petals.*—Five, no double blossoms observed.
*Petal arrangement.*—Non-overlapping at full bloom.
*Petal shape.*—Oval.
*Petal margin.*—Entire, slightly wavy.
*Average petal diameter.*—7/16" [11.1 mm.].
*Average petal length.*—⅝" [15.9 mm.].
*Petal apex.*—Rounded.
*Petal base.*—Slightly acute.
*Petal color.*—White [263. White] on both sides.
*Anther color.*—Brilliant yellow [83. brill.Y].
*Pollen production.*—Strong, enticing to bees.
*Pollen color.*—Brilliant yellow [83. brill.Y].
*Stigma color.*—Light greenish yellow [101. l.gY].
*Stigma position.*—Located about ⅛" [3.2 mm.] below the surrounding anthers.
*Stamen position.*—Typically located about 1/32" [0.8 mm.] below the petals.
*Average pistil length.*—½" [12.7 mm.].
*Average stamen length.*—7/16" [11.1 mm.].
*Ovary.*—Non-pubescent.
*Sepal color.*—Brilliant yellow green [116. brill.YG] on both sides.
*Sepal outer surface.*—Very slightly pubescent.
*Sepal length.*—3/16" [4.8 mm.].
*Sepal width.*—⅛" [3.2 mm.].
*Sepal apex.*—Rounded to elliptical to match the width and length.
*Sepal margin.*—Finely serrate.
*Fragrance.*—Moderate.
*Bloom density.*—Heavy.
*Number per cluster.*—2 to 5.
*Blooming period.*—Medium, blooms about three days after 'Blackred V' (U.S. Plant Pat. No. 19,576) interspecific fruit tree.
*Onset of bloom.*—One percent on Feb. 18, 2021.
*Date of full bloom.*—Feb. 27, 2021.
*Duration of bloom.*—One to two weeks, dependent on ambient temperature.

FRUIT

Maturity when described: Firm ripe, Jun. 19, 2021.
Date of first picking: Jun. 14, 2021.
Date of last picking: Jun. 24, 2021.
Size: Uniform, medium to large.
*Average diameter axially.*—2¼" [57.2 mm.].
*Average diameter across cheek plane.*—2¾" [69.9 mm.].
*Average diameter across suture plane.*—2 11/16" [68.3 mm.].
*Typical weight.*—5.8 ounces [164 grams].
Form: Uniform, oblate, symmetrical.
*Longitudinal section form.*—Oblate.
*Axial view form.*—Round.
Suture: A distinct Grayish purplish pink [253. gy.pPk] line located in a very shallow trough extending from the base to the pistil point.
Ventral surface: Rounded, slightly lipped on both sides.
Lips: Fairly equal.
Cavity: Flaring.
*Depth.*—7/16" [11.1 mm.].
*Breadth.*—1⅛" [28.6 mm.].
*Stem markings.*—Usually absent, Grayish yellow [90. gy.Y] when present.
Base: Truncate, somewhat cordate if viewed parallel to the suture.
Apex: Rounded to somewhat truncate.
Pistil point: An inconspicuous Pale yellow [89. p.Y] dot.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Moderate.
*Tendency to crack.*—None observed.
*Color.*—Very dark purplish red [260. v.d.pR] over a Dark red [16. d.R] background with very fine Pale yellow [86. p.Y] freckling throughout.
Flesh:
*Color.*—Very dark red [17. v.d.R] with Dark red [16. d.R] fibers throughout.
*Surface of pit cavity.*—Covered with Very dark red [17. v.d.R] fibers when twisted from the stone.
*Amygdalin.*—Moderate.
*Juice.*—Abundant, rich.
*Texture.*—Firm, crisp.
*Fibers.*—Abundant, fine, tender.
*Ripens.*—Fairly even.
*Flavor.*—A tasty blend of acid and sugar, typically 16 to 17 brix.
*Aroma.*—Very slight.
*Eating quality.*—Very good.

STONE

Type: Clingstone.
Form: Oval.
Hilum: Narrow.
Base: Rounded.
Apex: Rounded to slightly obtuse.
Tip: No protruding tip.
Sides: Fairly equal.
Surface: Rough with rounded ridges toward the base.
External color of stone: Light orange yellow [70. l.OY].
Pit wall color when cracked: Pale orange yellow [73. p.OY].
Cavity surface color: Strong yellowish brown [74. s.yBr].
Average pit wall thickness: 3/32" [2.4 mm.].
Average length: 1" [25.4 mm.].
Average width: 13/16" [20.6 mm.].
Average breadth: ⅜" [9.5 mm.].
Tendency To split: None observed.
Kernel:
*Form.*—Oval.
*Skin color.*—Pale yellow [89. p.Y].
*Pellicle color.*—Dark olive brown [96. d.OlBr].
*Vein color.*—Light olive brown [94. l.OlBr].
*Taste.*—Bitter.
*Viable.*—Yes.

*Average length.*—5/8" [15.9 mm.].
*Average width.*—7/16" [11.1 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Blackred VI' interspecific tree (U.S. Plant Pat. No. 23,718), by being self-unfruitful and by producing fruit that is dark purplish red in skin color, that is oblate in shape, that is clingstone in type, that is firm in texture, and that is very good in flavor, but is distinguished therefrom by blooming in the mid season instead of early season and by producing fruit that is larger in size, that is much darker red in flesh color, and that matures about 7 days earlier.

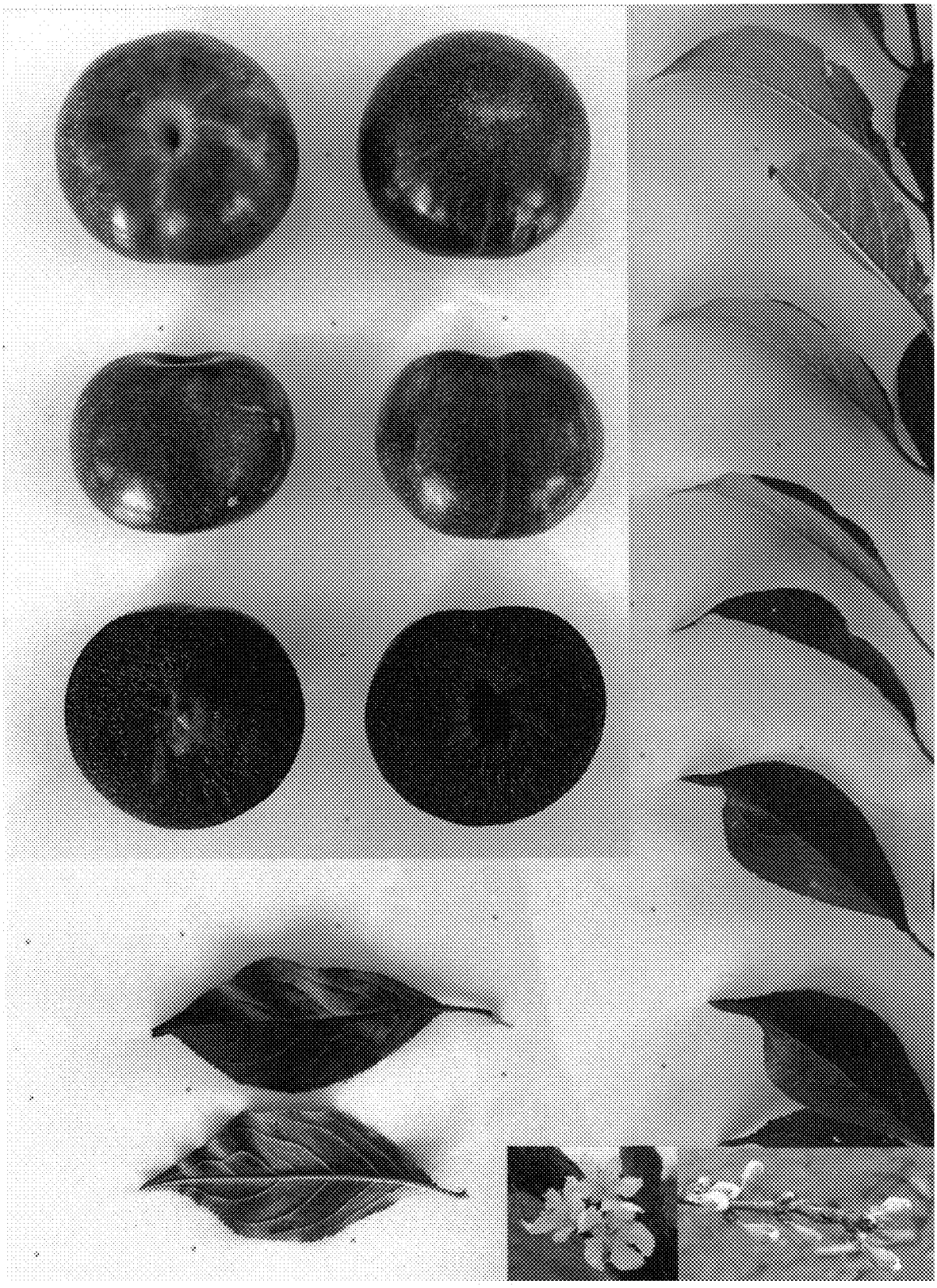

* * * * *